US00PP30444P3

(12) United States Plant Patent
Olesen

(10) Patent No.: US PP30,444 P3
(45) Date of Patent: Apr. 30, 2019

(54) GROUND COVER ROSE PLANT NAMED 'POULCOT014'

(50) Latin Name: ***Rosa* hybrid**
Varietal Denomination: Poulcot014

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 22 days.

(21) Appl. No.: 15/731,985

(22) Filed: Sep. 5, 2017

(65) Prior Publication Data

US 2019/0075692 P1 Mar. 7, 2019

(51) Int. Cl.
*A01H 5/02* (2018.01)

(52) U.S. Cl.
USPC ..... Plt./108
CPC ..... *A01H 5/02* (2013.01)

(58) Field of Classification Search
USPC ..... Plt./108
See application file for complete search history.

(56) References Cited

PUBLICATIONS

UPOV hit on rose plant named 'Poulcot014', QZ PBR 49231, filed Sep. 19, 2016.*

* cited by examiner

*Primary Examiner* — Anne Marie Grunberg

(57) ABSTRACT

A new garden rose plant of the Ground Cover class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcot014'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2008 and the resulting seeds were planted in a controlled environment in Fredensborg, Denmark. The new variety, named 'Poulcot014', originated as a single seedling from the stated cross.

The new variety may be distinguished from its male pollen parent and female seed parent primarily by the following characteristics. The male pollen parent plant grows to a height of 80 cm while the new variety grows to a height of 55 cm. The female seed parent plant has double petaled flowers while the new variety has single petaled flowers.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulcot014' from all other varieties of which we are aware.

As part of the rose development program, Mogens N. Olesen germinated the seeds from the aforementioned hybridization during winter of 2008 and conducted evaluations on the resulting seedlings in a controlled environment in Fredensborg, Denmark. 'Poulcot014' was selected in the spring of 2009 by the inventor as a single plant from the progeny of the aforementioned hybridization.

Asexual reproduction of 'Poulcot014' by rooted cuttings was first done by Mogens N. Olesen in the nursery in Fredensborg, Denmark in July, 2009. This initial and other subsequent asexual propagations conducted in controlled environments have demonstrated that the characteristics of 'Poulcot014' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcot014'.

Specifically illustrated in FIG. 1 of the drawings are open flowers, petals detached, sepals detached, showing reproductive flower parts and receptacle.

Figure 1:
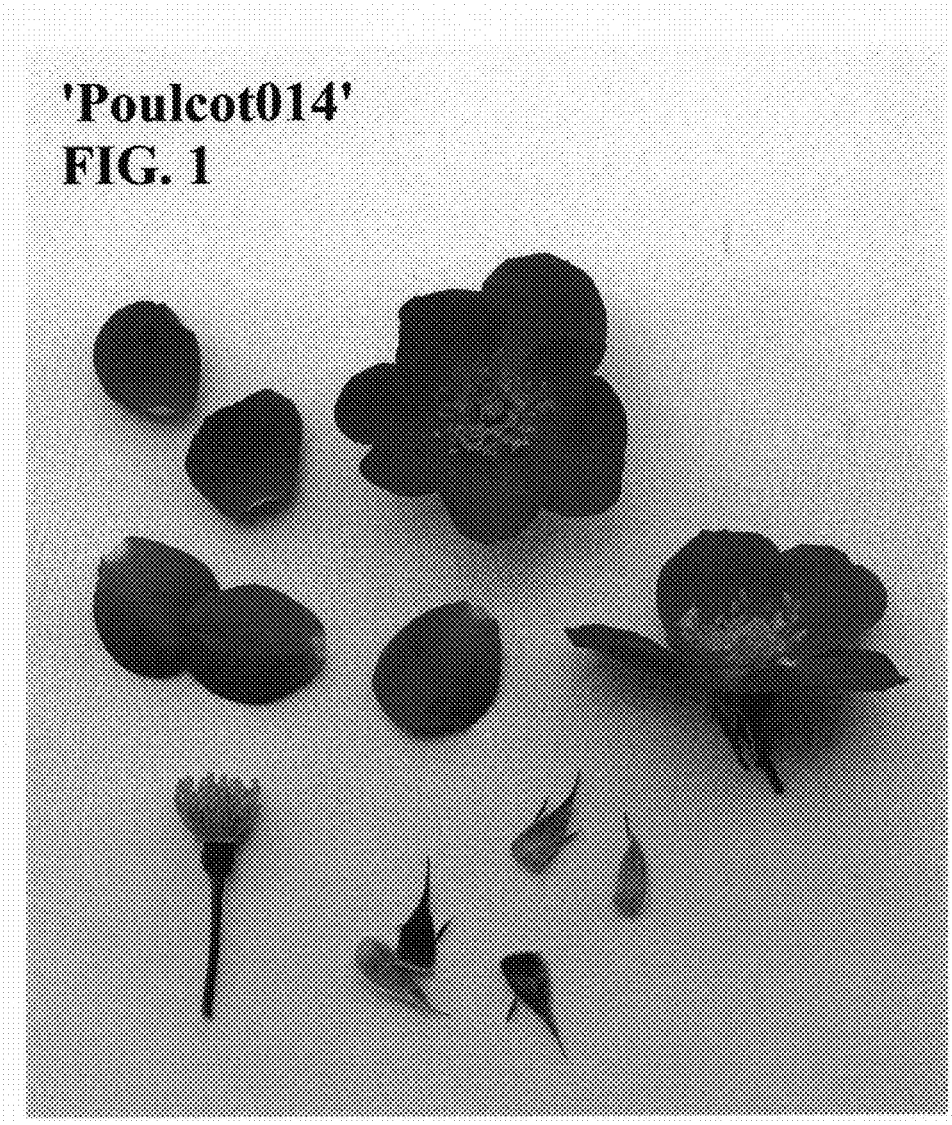
Figure 2:
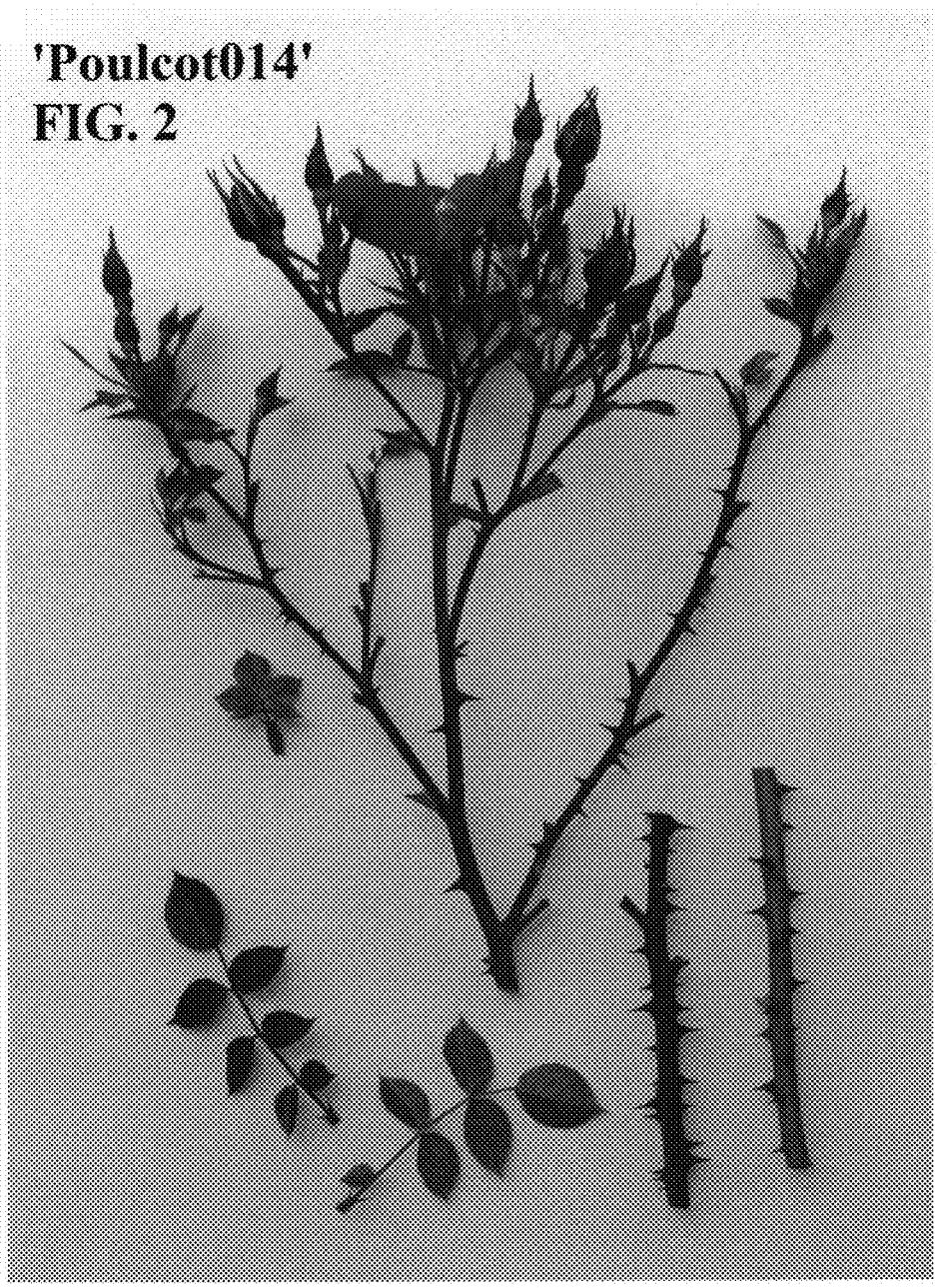

Specifically illustrated in FIG. 2 is a flowering branch, showing peduncles and flower buds, as well as bare stems and leaves. Plants shown are 2 years of age.

DETAILED DESCRIPTION OF THE VARIETY

The following is a description of 'Poulcot014', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcot007', U.S. Plant Pat. No. 16,985 are compared to 'Poulcot014' in Chart 1.

CHART 1

| | 'Poulcot014' | 'Poulcot007' |
|---|---|---|
| Petal Count | 5 to 6 | 20 |
| Flower Diameter | 55 mm | 40 mm |
| General Tonality of Flower Color | Red Group 45A. | Red Group 45B |

FLOWER AND FLOWER BUD

Blooming habit: Continuous.

Flower bud:

*Size*.—Upon opening, 24 mm in length from base of receptacle to end of bud. Bud diameter is 9 mm.

*Bud form*.—Ovoid.

*Bud color*.—As sepals divide petals are Red Group 46A.

*Sepal inner surface*.—Color: Yellow-Green Group 146B. Surface: Lightly pubescent.

*Sepal outer surface*.—Color: Yellow-Green Group 146A with intonations of Greyed-Purple Group 183B. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—22 mm long, 6 mm wide.

*Receptacle*.—Texture: Smooth. Size: 5 mm in height, 4 mm wide. Color: Yellow-Green Group 146B with intonations of Greyed-Purple Group 183B. Shape: Elliptical.

*Pedicel*.—Surface: Smooth. Length: 30 mm. Diameter: 2 mm on average. Color: Yellow-Green Group 144B with intonations of Greyed-Purple Group 185B. Strength: Strong.

*Peduncle*.—Length: 5 to 27 cm. Diameter: About 4 mm. Color: Yellow-Green Group 144A with intonations of Greyed-Purple Group 187B. Texture: Smooth.

Flower bud development: Flower buds are borne in clusters of 5 to 7 flower buds on each peduncle, developing in panicle form.

Flower bloom:

*Fragrance*.—Light floral.

*Duration*.—The blooms have a duration on the plant of approximately 5 days. Petals fall cleanly away from plant after flowers have fully matured.

*Size*.—Flower diameter is 55 mm when open. Flower depth is 10 mm.

*Flower shape*.—Single flower which is fully open and almost flat.

Petalage: Under normal conditions, flowers have 5 to 6 petals.

General tonality of flower: Open flowers are Red Group 45A. At the base, Yellow Group 7B.

Petal color: Upper surface is Red Group 45A with basal spot Yellow Group 7B. Lower surface is Red Group 53B with a basal spot of Yellow Group 8B.

Petals:

*Petal reflex*.—None.

*Margin*.—Entire and uniform. Occasional cleft. Weak undulations.

*Shape*.—Elliptic. Apex shape: Rounded. Base shape: Rounded.

*Size*.—29 mm (l)×27 mm (w).

*Texture*.—Smooth.

*Thickness*.—Average.

Petaloids: None.

*Color*.—

Reproductive flower parts:

*Pollen*.—Color: Yellow Group 13A. Quantity: Moderate.

*Anthers*.—Size: 2 mm in length. Color: Yellow-Orange Group 16A. Quantity: 50 on average.

*Filaments*.—Color: Yellow Group 12A. Length: 4 mm.

*Pistils*.—Length: 4 mm. Quantity: 20 on average.

*Stigmas*.—Color: Greyed-Yellow Group 160D.

*Styles*.—Color: Greyed-Purple Group 186B.

*Location of stigmas*.—Inferior in location relative to the length of the filaments and the height of the anthers.

*Hips*.—None Observed.

PLANT

Plant growth: Low growing, spreading. Plants are 55 cm in height, and 50 cm wide.

Stems:

*Color of juvenile growth*.—Yellow-Green Group 144A with intonations of Greyed-Purple Group 187A.

*Color of mature growth*.—Yellow-Green Group 146B.

*Length*.—Canes are about 25 cm from the base of the plant to the flowering portion.

*Diameter*.—About 6 mm.

*Internodes*.—On mature canes about 40 mm between nodes.

*Surface texture*.—Young wood: Smooth. Older wood: Smooth.

Long prickles:

*Incidence*.—12 prickles per 10 cm of stem.

*Size*.—Average length of prickles on mature stems is 7 mm.

*Shape*.—Upper portion is linear. Lower portion is concave.

*Color*.—Juvenile prickles: Greyed-Purple Group 183B. Mature prickles: Greyed-Purple Group 183B.

Plant foliage:

*Compound leaf*.—100 mm (l)×60 (w).

*Quantity*.—2 leaves per 10 cm of stem on average.

*Leaf bearing angle to the stem*.—45 degrees.

*Color of juvenile foliage*.—Upper side: Yellow-Green Group 144A with intonations of Greyed-Purple Group 183B at margins. Lower side: Yellow-Green Group 146C.

*Color of mature foliage*.—Upper side: Yellow-Green Group 147A. Lower side: Yellow-Green Group 146B.

Plant leaves and leaflets:

*Stipules*.—Size: 10 mm long, 3 mm wide. Quantity: 2 per compound leaf. Shape: Linear, slightly broad based with outward extending apices. Margins: Finely serrated. Color: Yellow-Green Group 146B with intonations of Greyed-Purple Group 183B.

*Petiole*.—Length: 10 mm. Diameter: 1.5 mm. Upper surface color: Greyed-Purple Group 187A. Lower surface color: Yellow-Green Group 144A.

*Rachis*.—Length: 50 mm. Upper surface color: Greyed-Purple Group 187A. Lower surface color: Yellow-Green Group 144A.

*Leaflet*.—Quantity: Normally 7 leaflets. Margins: Serrated. Size: Terminal leaflets are about 35 mm long, 28 mm wide. Shape: Generally elliptical. Base: Rounded. Apex: Cuspidate. Texture: Smooth. Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Ground Cover rose class named 'Poulcot014', substantially as illustrated and described herein, due to its abundant red flowers, disease resistance, and extended period of bloom.

* * * * *

'Poulcot014'

'Poulcot014'